(12) United States Patent
Takatsuji et al.

(10) Patent No.: US 6,215,043 B1
(45) Date of Patent: Apr. 10, 2001

(54) METHOD FOR SHORTENING INTERNODE OF INFLORESCENCE BY INTRODUCING GENE FOR PETUNIA TRANSCRIPTION FACTOR PETSPL2

(75) Inventors: Hiroshi Takatsuji, Tsukuba; Hitoshi Nakagawa, Inashiki-gun, both of (JP)

(73) Assignee: Director General of National Institute of Agrobiological Resources, Ministry of Agriculture, Forestry and Fisheries, Ibaragi (JP)

( * ) Notice: Subject to any disclaimer, the term of this patent is extended or adjusted under 35 U.S.C. 154(b) by 0 days.

(21) Appl. No.: 09/156,580

(22) Filed: Sep. 18, 1998

(30) Foreign Application Priority Data

Aug. 7, 1998 (JP) .................................................. 10-224852

(51) Int. Cl.$^7$ ............................. C12N 15/29; C12N 5/04; C12N 15/82; C12N 15/90; A01H 5/00
(52) U.S. Cl. .................... 800/290; 435/69.1; 435/320.1; 435/468; 536/23.6; 800/278; 800/298; 800/317; 800/323.1
(58) Field of Search ................................ 435/69.1, 320.1, 435/410, 419, 430, 468; 800/278, 290, 295, 298, 317, 323.1; 536/23.6

(56) References Cited

FOREIGN PATENT DOCUMENTS

WO 90/12084    10/1990  (WO) .............................. C12N/5/00

OTHER PUBLICATIONS

Takatsuji, Hiroshi. "Transcription Factors Controlling Floral Organ Development." *Cell Technology.* Plant Technology Series. Shujunsha, Japan, pp. 96–106.
Takatsuji, Hiroshi. *The IDEN,* vol. 51, No. 4, pp. 34–38 (1997).
Torii, K.U. et al. *Plant Cell,* vol. 8, pp. 735–746 (1996).
Dehio et al. *Plant Mol. Bio.,* vol. 23, pp. 1199–1210 (1993).
Sakai, Hajime et al. "Role of Superman in maintaining *Arabidopsis* floral whorl boundaries." *Nature,* vol. 378, pp. 199–203 (1995).
Bancroft, E. et al. (The EU Arabidopsis Genome Project: Mt. Bevan) Analysis of 1.9 Mb of contiguous sequence for chromosome 4 of *Arabidopsis thaliana. Nature,* vol. 391, pp. 485–488 (1998).
Ken–ichi Kubo, et. al.: "$Cys_2/His_2$ zinc–finger protein family of petunia: evolution and general mechanism of target–sequence recognition" *Nucleic Acids Research* vol. 26, No. 2 pp. (608–615).

*Primary Examiner*—Gary Benzion
*Assistant Examiner*—Ashwin D. Mehta
(74) *Attorney, Agent, or Firm*—Townsend & Townsend & Crew LLP (57) ABSTRACT

A gene encoding DNA which is selected from a) or b): a) DNA having a nucleotide sequence from the 190th position to the 807th position of a nucleotide sequence represented in SEQ ID NO: 1 of the Sequence Listing; or b) DNA which hybridizes to DNA of a) under stringent conditions, and encodes a transcription factor capable of altering characters of a plant.

12 Claims, 5 Drawing Sheets

FIG. 1

```
CCCAGTGCCA TTTTTTCTCT CTAGTCAAGC TCTCTATATC ATCATCACTA TTCCCTTGGC

TGCAGTAACA CTCCTATTTA ACCCTCACAA AAAAATTACC AGAGGGCAGC AAAAAATGCT

TGAACATAAT TATTATACTT ACTATTAAGC TAGATTTCCT CTTGATCTTG CTAGGTTTGA

CTGGAGAAAA TGGCAGGCAT GGATAGAAAC AGTTTCAACA GTAAGTACTT CAAAAACAAA
             M   A  G  M   D  R  N    S  F  N  S   K  Y  F    K  N  K

AGCATCATGG CAAGACAGAT GGAGTACTTG AATAACAACA ATGGCGACAA TAACAACAAC
 S  I  M  A   R  Q  M    E  Y  L    N  N  N  N    G  D  N    N  N  N

AATAATGTTA CAAGCTCATT ACGAGATAAT TATGGAAATG AAGATCATTT ACTTGGTGGA
 N  N  V  T   S  S  L    R  D  N    Y  G  N  E    D  H  L    L  G  G

CTATTCTCTT GGCCTCCAAG ATCTTATACA TGTAGCTTTT GTAAAAGGGA ATTTAGATCT
 L  F  S  W   P  P  R    S  Y  T    C  S  F  C    K  R  E    F  R  S

GCTCAAGCTC TTGGTGGACA CATGAATGTT CATAGAAGAG ATAGAGCCAT TTTGAGACAA
 A  Q  A  L   G  G  H    M  N  V    H  R  R  D    R  A  I    L  R  Q

TCACCACCTA GAGATATTAA TAGGTATTCT CTTCTAAACC TTAATCTTGA ACCAAACCCT
 S  P  P  R   D  I  N    R  Y  S    L  L  N  L    N  L  E    P  N  P

AACTTTTACC CTAGTCATAA CCCTAGTTTT TCAAGAAAAT TCCCACCTTT TGAAATGAGG
 N  F  Y  P   S  H  N    P  S  F    S  R  K  F    P  P  F    E  M  R

AAATTAGGAA AAGGAGTTGT TCCAAACAAT CACTTGAAAA GTGCCAGAGG GCGTTTTGGA
 K  L  G  K   G  V  V    P  N  N    H  L  K  S    A  R  G    R  F  G

GTTGAGAAAA TTGACTCTTT CATGCAAGAA AAAGAATGTA CTACTACAGT GATCAAGAAG
 V  E  K  I   D  S  F    M  Q  E    K  E  C  T    T  V  I    K  K

TCCGAGTTTC TAAGATTGGA CTTGGGAATT GGGTTGATCA GTGAATCAAA GGAAGATTTA
 S  E  F  L   R  L  D    L  G  I    G  L  I  S    E  S  K    E  D  L

GATCTTGAAC TTCGACTGGG ATCCACTTAA CTATATCTAA TTTTTACGGC ATTAAGGTTT
 D  L  E  L   R  L  G    S  T

GTAAATTGAG TCCACAGCTT AGTCAAAACT ACTTATGCAC TTTAATATGG CTTCTTGTGC

TATATTTATT TATTTTACAT GGCTGTATCT AGGTTTGCAT TTTAAGATTT AGTACCTTGT

CAGATTAAAA GAAAACGAAA GTTAAATTAA AAAAAAA
```

METHOD FOR SHORTENING INTERNODE OF INFLORESCENCE BY INTRODUCING GENE FOR PETUNIA TRANSCRIPTION FACTOR PETSPL2

BACKGROUND OF THE INVENTION

1. Field of the Invention

The present invention relates to a gene encoding a transcription factor capable of altering characters of a plant and its use. More particularly, the present invention relates to the PetSPL2 gene which is a novel gene derived from *Petunia hybrida,* genes related thereto, and the use thereof.

2. Description of the Related Art

In order to clarify regulatory mechanisms controlling the characters of a plant, for example, morphogenesis of a flower, molecular biological and molecular geneticical studies have been conducted using *Arabidopsis thaliana, Antirrhinum majus,* and *Petunia hybrida.* In particular, *Petunia hybrida* is preferably used as a subject of studies for the following reasons: high value as a horticultural plant; the presence of various species; ease of transformation; ease to observe due to its large flower; and accumulation of genetical findings (H. Takatsuji, *"Molecular mechanism for determining a shape of a plant",* Cell Technology, Plant Cell Technology Series (SHUJUNSHA), pp. 96–106).

Genes which cause mutation have been isolated from mutants in which floral organs of the above-mentioned plant is altered. As a result, it is becoming clear that transcription factors play important roles in differentiation and morphogenesis of a flower. For example, SUPERMAN of *Arabidopsis thaliana* is a transcription factor having a zinc finger motif as a DNA binding domain. It is known that, in SUPERMAN mutant with its gene mutated, number of stamens are remarkably increased, and pistils are defective (*THE IDEN,* April, 1997 (Vol. 51, No. 4), pp. 34–38).

For understanding the mechanism for the control of characters of a plant, it is important to identify a novel transcription factor which is involved in such control. A gene for a transcription factor which controls morphogenesis of a flower may be introduced into a plant by using gene engineering procedure. It is possible to obtain a plant, using gene introduction, having a flower with novel characters which has not been obtained or is not likely to be obtained by a conventional breeding. It is considered that a plant with such novel characters is horticulturally valuable.

SUMMARY OF THE INVENTION

A gene of the present invention has DNA which is selected from a) or b): a) DNA having a nucleotide sequence from the 190th position to the 807th position of a nucleotide sequence represented in SEQ ID NO:1 of the Sequence Listing; or b) DNA which hybridizes to DNA of a) under stringent conditions, and encodes a transcription factor capable of altering characters of a plant.

A gene of the present invention encodes a transcription factor which is selected from i) or ii): i) a transcription factor having an amino acid sequence from the 1st position to the 206th position of an amino acid sequence represented in SEQ ID NO:2; or ii) a transcription factor having an amino acid sequence in which one or more amino acids of i) are subjected to deletion, substitution, or addition, and being capable of altering characters of a plant.

In one embodiment of the present invention, the characters of a plant include one selected from the group consisting of the height of a plant and the length of an internode.

A method for producing a transgenic plant of the present invention includes the steps of: introducing a plant cell with the above-mentioned gene; and regenerating a plant body from the plant cell having the introduced gene.

In one embodiment of the present invention, the plant belongs to dicotyledon.

In another embodiment of the present invention, the plant belongs to Solanaceae.

In another embodiment of the present invention, the plant belongs to Petunia.

In another embodiment of the present invention, the gene is incorporated into a plant expression vector.

A transgenic plant of the present invention is produced by the above-mentioned method.

Thus, the invention described herein makes possible the advantages of (1) providing a gene encoding a transcription factor capable of altering characters of a plant, in particular, a height of a plant and a length of an internode; (2) providing a method for producing a plant with its character altered by introduction of the gene; and (3) providing a transgenic plant.

These and other advantages of the present invention will become apparent to those skilled in the art upon reading and understanding the following detailed description with reference to the accompanying figures.

DESCRIPTION OF THE PREFERRED EMBODIMENTS

Hereinafter, the present invention will be described in detail.

The term "transcription factor" as used herein refers to a protein which binds to a DNA regulatory region of genes to control the synthesis of mRNA. Some transcription factors are known to have a highly conservative amino acid sequence called zinc finger motif in their DNA binding domains.

A gene of the present invention encodes a transcription factor capable of altering characters of a plant. This gene may have either of the following DNAs:

a) DNA having a nucleotide sequence from the 190th position to the 807th position of a nucleotide sequence represented in SEQ ID NO:1 of the Sequence Listing; or b) DNA which hybridizes to DNA of a) under stringent conditions, and encodes a transcription factor capable of altering characters of a plant.

The gene of the present invention may also have DNA which encodes a transcription factor capable of altering characters of a plant, and has a homology of about 60% or more, preferably about 70% or more, more preferably about 80% or more, and still more preferably about 90% or more, with DNA of a).

Preferably, the gene of the present invention may contain DNA of a).

The gene of the present invention may also encode either of the following transcription factors:

i) a transcription factor having an amino acid sequence from the 1st position to the 206th position of an amino acid sequence represented in SEQ ID NO:2; or ii) a transcription factor having an amino acid sequence in which one or more amino acids of i) are subjected to deletion, substitution, or addition, and being capable of altering characters of a plant.

The number of amino acids subject to deletion, substitution, or addition may be about 130 or less, preferably about 60 or less, more preferably about 30 or less, still more preferably about 20 or less, and still further more preferably 10 or less.

Preferably, the gene of the present invention may encode the transcription factor of i).

Figure 1:
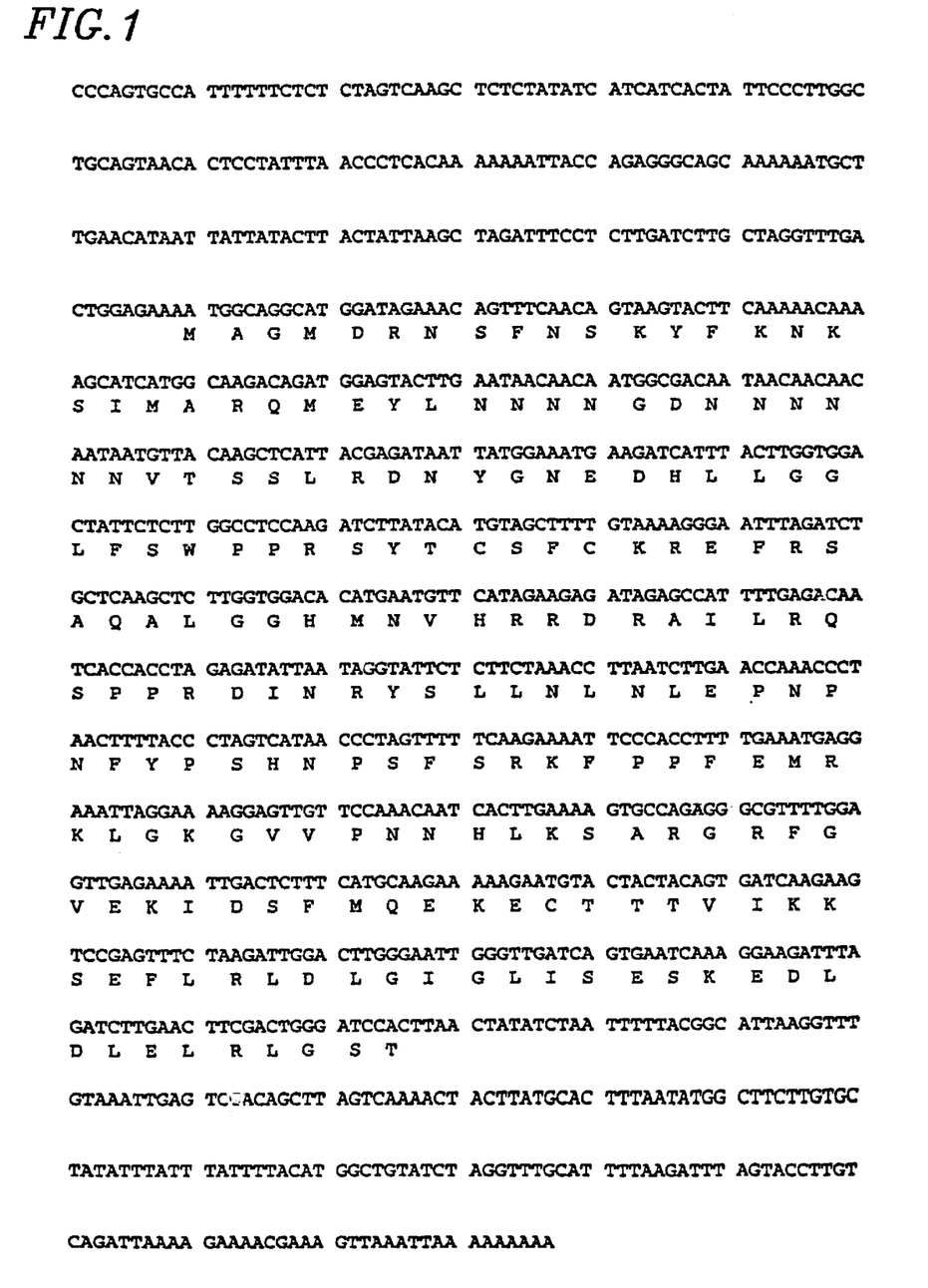
FIG. 1 shows a nucleotide sequence (SEQ ID NO:1) of PetSPL2 gene and its deduced amino acid sequence (SEQ ID NO: 2).

The particularly preferred gene in the present invention is PetSPL2 gene. FIG. 1 shows a cDNA sequence (SEQ ID NO:1) of this gene and its deduced amino acid sequence (SEQ ID NO:2).

Alterations in "characters of a plant" refer to any changes in at least one character of a plant. The character of a plant includes, but is not limited to, at least one of the height of a plant and the length of an internode of a plant. These changes are evaluated by comparing the characters of a plant obtained by introducing a gene of the present invention with the characters of a plant (wild-type or horticultural type) before introducing the gene.

Examples of height change of a plant include, but are not limited to, a dwarf and a semi-dwarf. The dwarfism is preferably about ½ or less, more preferably about ⅓ or less of a standard height of a plant before introducing the gene.

An example of length change of an internode includes, but is not limited to, a reduction of an internode. The reduction of an internode includes any reduction of an internode of a reproductive branch (i.e., inflorescence) and an internode of a vegetative branch (i.e., phyllotaxis). The reduction of inflorescence is a particularly preferable example of a change. The change in length of an internode preferably acheieves a length of about ½ or less, more preferably about ⅓ or less, and most preferably about 1/10 or less, compared with a standard internode of the plant before introducing a gene.

An example of changed characters of a plant is a combination of a drawf and a reduction of an internode, more preferably a combination of a drawf and a reduction of an internode of an inflorescence.

The gene of the present invention can be isolated, for example, by performing polymerase chain reaction (PCR) with genomic DNA of a plant as a template, using a pair of degenerated primers corresponding to a conserved region of the amino acid sequence encoded by a gene of a known transcription factor, and screening a genomic library of the same plant, using the amplified DNA fragment thus obtained as a probe. Examples of a pair of primers include a combination of 5'-CARGCNYTNGGNGGNCAY-3' (SEQ ID NO:3) or 5'-YTNGGNGGNCAYATGAAY-3' (SEQ ID NO:4) with 5'-ARNCKNARYTCNARRTC-3' (SEQ ID NO:5) in which N is inosine, R is G or A, Y is C or T, and K is T or G.

PCR can be performed in accordance with the manufacturer's instructions for a commercially available kit and instruments, or by a procedure well known to those skilled in the art. A method for producing a gene library, stringent conditions used for hybridization with a probe, and a method for cloning a gene are well known to those skilled in the art. For example, see Maniatis et al., *Molecular Cloning, A Laboratory Manual, 2nd Ed.,* Cold Spring Harbor Laboratory Press, Cold Spring Harbor, N.Y. (1989).

A nucleotide sequence of the gene thus obtained can be determined by a nucleotide sequence analysis method known in the art or by a commercially available automatic sequencer.

The gene of the present invention is not limited to those isolated from native genome but may include synthetic polynucleotides. Synthetic polynucleotides can be obtained, for example, by modifying a sequenced gene as described above using a procedure well known to those skilled in the art.

The gene of the present invention can be ligated to an appropriate plant expression vector by a method well known to those skilled in the art and introduced into a plant cell by a known gene recombination technique. The introduced gene is incorporated into the DNA of a plant cell. The DNA of a plant cell includes DNA contained in various organelles (e.g., mitochondria, chloroplasts, etc.) of a plant cell, as well as chromosomes.

The "plant" includes both *monocotyledon* and *dicotyledon*. The preferred plant is *dicotyledon*. The *dicotyledon* includes both Archichlamiidae and Sympetalidae. A plant of Sympetalidae is preferable. Examples of the plants of Sympetalidae include Gentianales, Solanales, Lamiales, Callitrichales, Plantaginales, Campanulales, Scrophulariales, Rubiales, Dipsacales, Asterales, and the like. A plant of Solanales is preferable. Examples of the plants of Solanales include Solanaceae, Hydrophyllaceae, Polemoniaceae, Cuscutaceae, Convolvulaceae, and the like. Solanaceae is preferable. Solanaceae includes Petunia, Datura, Nicotiana, Solanum, Lycopersicon, Capsicum, Physalis, and Lycium, etc. Plants of Petunia, Datura, and Nicotiana are preferable. Petunia is more preferable. Examples of the plants of Petunia include *P. hybrida, P. axillaris, P. inflata, P. violacea,* and the like. A plant of *P. hybrida* is especially preferable. The "plant" refers to a plant body having a flower and/or a fruit and a seed obtained from it, unless otherwise specified.

Examples of the "plant cell" include cells from plant organs such as leaves and roots, callus, and suspension cultured cells.

The term "plant expression vector" as used herein refers to a nucleic acid sequence in which various regulatory elements, such as a promotor, for regulating expression of the gene of the present invention, are linked to each other so as to be operable in a host plant cell. Preferably, the plant expression vector may include a plant promoter, a terminator, a drug resistant gene and an enhancer. It is well known to those skilled in the art that a type of the plant expression vector and regulator elements may be varied depending on the type of host cell. A plant expression vector used according to the present invention may further contain a T-DNA region. The T-DNA region allows a gene to be efficiently introduced to plant genome especialy when Agrobacterium is used to transform a plant.

The term "plant promoter" as used herein refers to a promoter that functions in a plant. Constitutive promoters as well as tissue-specific promoters which selectively function in a part of a plant body, including a flower, are preferable. Examples of plant promoters include, but are not limited to, Cauliflower mosaic virus (CaMV) 35S promoter and a promoter of nopaline synthase.

The term "terminator" as used herein refers to a sequence positioned downstream of a region of a gene encoding a protein, which is involved in the termination of transcription of mRNA, and the addition of a poly A sequence. The terminator is known to contribute to the stability of mRNA, thereby affecting the expression level of a gene. Examples of such terminators include, but are not limited to, CaMV 35S terminator and a terminator of a nopaline synthase gene (Tnos).

A "drug resistant gene" is desirable to facilitate the selection of transgenic plants. The examples of such drug resistant genes for use in the invention include, but are not limited to, a neomycin phosphotransferase II (NPTII) gene for conferring kanamycin resistance, and a hygromycin phosphotransferase gene for conferring hygromycin resistance.

An "enhancer" may be used to enhance the expression level of a gene of interest. As the enhancer, an enhancer region containing a sequence upstream of the above-mentioned CaMV 35S promoter is preferable. More than one enhancers may be used in one plant expression vector.

The plant expression vector according to the present invention may be produced by using a recombinant DNA technique well known to those skilled in the art. The examples of preferable vectors for constructing a plant expression vector include, but are not limited to pBI-type vectors or pUC-type vectors.

A plant expression vector may be introduced into a plant cell by using methods well known to those skilled in the art, for example, a method of infecting a plant cell with Agrobacterium or a method of directly introducing a vector into a cell. The method using Agrobacterium may be performed, for example, as described in Nagel et al., *Microbiol. Lett.*, 67, 325, 1990. According to this method, Agrobacterium is first transformed with a plant expression vector by, for example, electroporation, and then the transformed Agrobacterium is infected to a plant cell by a well-known method such as a leaf-disk method. Examples of the methods for directly introducing a plant expression vector into a cell include, but are not limited to, an electroporation method, a particle gun method, a calcium phosphate method, and a polyethylene glycol method. These methods are well known in the art and a method suitable for a particular plant to be transformed may be suitably selected by those skilled in the art.

The cells in which plant expression vectors have been introduced are selected based on their drug resistance such as resistance to kanamycin. Thereafter, the cells may be regenerated to a plant body by using a conventional method.

Expression of the introduced gene of the present invention in the regenerated plant body can be confirmed by using a procedure well known to those skilled in the art. This confirmation can be performed by northern blot analysis, for example. More specifically, the total RNAs may be extracted from leaves of a resultant plant, and may be subjected to denatured agarose gel electrophoresis, and then, RNAs may be blotted onto an appropriate membrane. The blot can be hybridized with a labelled RNA probe complementary to a part of the introduced gene to detect mRNA from the gene of the present invention.

The plant of the present invention is a transgenic plant produced by the above-mentioned procedure. It is preferable that the altered characters of the transgenic plant (i.e., a height of a plant and/or a length of an internode) include that which is not found in a known wild-type or horticultural type. It is also preferable that the altered characters of a plant are horticulturally valuable. Furthermore, it is preferable that altered characters of a plant are stably conserved over subsequent generations.

EXAMPLES

Hereinafter, the present invention will be described by way of the following illustrative examples. Restriction enzymes, plasmids and the like used in the following examples are available from commercial sources.

Example 1
Isolation of PetSPL2 Gene

The protein encoded by the SUPERMAN gene of *Arabidopsis thaliana* was compared with the protein encoded by the GmN479 gene (Kouchi et al., personal communication) expressed specifically in soy bean root nodules. Three different degenerate primers for use in PCR were synthesized based on the amino acid sequences commonly present in both proteins. The nucleotide sequences of two primers oriented 5' to 3' in the genes are 5'-CARGCNYTNGGNGGNCAY-3' (primer 1, corresponding to an amino acid sequence QALGGH; SEQ ID NO:6) and 5'-YTNGGNGGNCAYATGAAY-3'(SEQ ID NO:4). (Primer 2, corresponding to an amino acid sequence LGGHMN; SEQ ID NO:7), respectively, and a nucleotide sequence of a primer oriented 3' to 5' in the genes is 5'-ARNCKNARYTCNARRTC-3' (SEQ ID NO:5) (primer 3, corresponding to an amino acid sequence DLELRL; SEQ ID NO:8), wherein N is inosine, Y is either C or T, R is either G or A, and K is either T or G.

A first set of PCR was conducted with primer 1 and primer 3 under the following conditions: 94° C. for 10 minute, followed by 30 cycles of 94° C. for 30 seconds, 50° C. for 30 seconds and 72° C. for 60 seconds, and subsequently 72° C. for 7 minutes, using as a template a genomic DNA of a petunia (*Petunia hybrida* var. Mitchell) extracted according to the method described in Boutry, M. and Chua N. H. (1985) *EMBO J.* 4, 2159–2165. In addition, a second PCR was conducted with primer 2 and primer 3, while using as a template a portion of the product from the first PCR. The reaction conditions were the same as those used in the first PCR. Amplified DNA fragments were inserted into the TA cloning vector (produced by Invitrogen), which were then introduced into *E. coli* according to a conventional method. Plasmids were extracted from the transformed *E. coil* and the nucleotide sequences of the DNA fragment was determined. The results revealed that a part of zinc finger motif contained in common in SUPERMAN and GmN479 was encoded within the resulting DNA fragment. The gene from which this DNA fragment was derived was designated as PetSPL2 gene. In the same series of experiments, the presence of 3 other DNAs (PetSPL1, 3 and 4 genes) containing a nucleotide sequence similar to that of PetSPL2 was demonstrated. For details regarding the PetSPL3 gene, see Japanese Patent Application No. 10-65921.

To clone cDNA of the PetSPL2 gene, the DNA fragment described above and a GENETRAP cDNA selection kit (produced by BRL) were used to screen a cDNA library of petunia floral buds (*Petunia hybrida* var. Mitchell) which had been created, using the BRL kit, within a pSPORT plasmid vector (produced by BRL). Several clones for the PetSPL2 gene were obtained by screening this cDNA library. Thus, cDNA for the PetSPL2 gene derived from Petunia was isolated.

Example 2
Analysis of the Nucleotide Sequence and Amino Acid Sequence of PetSPL2 gene The longest clone out of the clones obtained in Example 1 contained a PetSPL2 gene cDNA fragment of about 1.0 kb. The DNA nucleotide sequence of this cDNA fragmet was determined (SEQ ID NO:1). From an open reading frame contained in the resulting DNA nucleotide sequence, an amino acid sequence of the protein was deduced (SEQ ID NO:2).

The comparison of the nucleotide sequences indicated that the PetSPL2 gene showed 58%, 67% and 51% nucleotide sequence homology to the SUPERMAN, PetSPL1 and PetSPL4 genes, respectively. The PetSPL2 gene showed 52% nucleotide sequence homology to PetSPL3 gene. This comparison of the nucleotide sequences was conducted only within the coding region of each gene.

The deduced amino acid sequence of PetSPL2 contained a single TFIIIA-type zinc finger motif similar to that of SUPERMAN. On this basis, it was presumed that PetSPL2 was a transcription factor. PetSPL2 showed about 37% and 23% homology to SUPERMAN and PetSPL3, respectively, in the full-length amino acid sequence.

Table 1 compares the amino acid sequence of SUPERMAN with that of each PetSPL in the zinc finger motif. Amino acid homology (about 100%) of PetSPL2 to SUPERMAN in the zinc finger motif was shown to be the same as the corresponding homology (about 100%) of PetSPL1 to SUPERMAN and to be higher compared with that (about 76%) of PetSPL3 to SUPERMAN (wherein the amino acid sequence homology was calculated assuming that the zinc finger motif extends from the 4th C to the 24th H). Table 1 also shows comparison of C terminal hydrophobic region of SUPERMAN with that of each PetSPL.

plasmid was further cleaved with AscI and PacI, and the resultant DNA fragment encoding PetSPL2 was introduced into AscI and PacI sites of a binary vector pBINPLUS (van Engelen, F. A. et al., (1995), supra).

Figure 2:
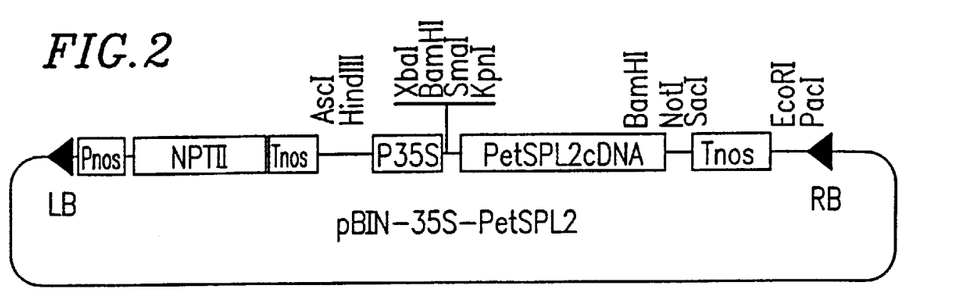
FIG. 2 is a schematic view showing a PetSPL2 high expression vector (pBIN-35S-PetSPL2).

The constructed PetSPL2 gene high expression vector (pBIN-35S-PetSPL2) includes, as shown in FIG. 2a, a CaMV 35S promoter region (P35S; 0.9 kb), a polynucleotide of the present invention encoding PetSPL2 (PetSPL2; 1.0 kb) and a terminator region of nopaline synthase (Tnos; 0.3 kb). In FIG. 2, Pnos and NPTII indicate a promoter region of nopaline synthase and neomycin phosphotransferase II gene, respectively. LB and RB indicate T-DNA left border and T-DNA right border, respectively.

Example 4
Introduction of the PetSPL2 Gene into PETUNIA Cells
(1) (Transformation of *Agrobacterium tumefaciens*)

*Agrobacterium tumefaciens* LBA4404 line (purchased from Clontech) was cultured in an L medium containing 250 μg/ml streptomycin and 50 μg/ml rifampicin at 28° C. According to the method of Nagel et al. (1990) (supra), a cell suspension of this strain was prepared. The PetSPL2 gene high expression vector constructed in Example 3 was introduced into the above described strain by electroporation.

(2) (Introduction of a polynucleotide encoding PetSPL2 into Petunia cell)

The *Agrobacterium tumefaciens* LBA4404 line obtained in (1) was cultured (at 28° C., 200 rpm) with agitation in YEB medium (D. M. Glover ed. *DNA Cloning*, IPL PRESS, second edition, p.78), followed by a 20-fold dilution with sterilized water. Leaf sections of petunia (*Petunia hybrida* var. Mitchell) were cultured in this diluted solution. After

TABLE 1

```
Zinc-finger
SUPERMAN    SYTCSFCKREFRSAQALGGHMNVHRRDRARLRLQQSPSSSSTP    (SEQ ID NO:9)
PetSPL1     SYTCSFCKREFRSAQALGGHMNVHRRDRARLRL-QSPPRENGT    (SEQ ID NO:10)
PetSPL2     SYTCSFCKREFRSAQALGGHMNVHRRDRAILR--QSPPRDINR    (SEQ ID NO:11)
PetSPL3     SYECNFCKRGFSNAQALGGHMNIHRKDKAKLKKQKQHQRQQKP    (SEQ ID NO:12)
PetSPL4     FYRCSFCKRGFSNAQALGGHMNIHRKDRAKLREISTDNLNIDQ   (SEQ ID NO:13)

C-terminal hydrophobic region
                 *    * *     *       *
SUPERMAN    ILRNDEIISLELEIGLINESEQDLDLELRLGFA    (SEQ ID NO:14)
PetSPL1     LMKRSEFLRLELGIGMINESKEDLDLELRLGYT    (SEQ ID NO:15)
PetSPL2     VIKKSEFLRLDLGIGLISESKEDLDLELRLGST    (SEQ ID NO:16)
PetSPL3     GSVDSRENRLPARNQETTPFYAELDLELRLGHE    (SEQ ID NO:17)
PetSPL4     CGTLDEKPKRQAENNDMQQDDSKLDLELRLGPD    (SEQ ID NO:18)
```

From the results described above, it was presumed that PetSPL2 is a novel transcription factor with a closer relationship to SUPERMAN than to PetSPL3, and belongs to a class different from that of PetSPL3.

Example 3
Construction of a Plant Expression Vector Containing a Polynucleotide Encoding PetSPL2

A DNA fragment (HindIII-XbaI fragment) containing a CaMV 35S promoter in a plasmid pBI221 (purchased from Clontech) and a DNA fragment (SacI-EcoRI fragment) containing a NOS terminator were sequentially inserted into a multicloning site of plasmid PUCAP (van Engelen, F. A. et al., *Transgenic Res.* 4:288–290 (1995)) to produce pUCAP35S. On the other hand, pSPORT/PetSPL2 plasmid containing PetSPL2 was cleaved at KpnI and SacI sites (which are the sites within this vector), and inserted between KpnI and SacI sites of the pUCAP35. This recombinant 2–3 days, the Agrobacterium was removed using a medium containing carbenicillin, and thereafter these leaf sections were subcultured in a selection medium by transferring to new media every 2 weeks. The Kanamycin resistance trait conferred by the expression of the NPTII gene derived from pBINPLUS, introduced together with the above-mentioned PetSPL2 gene, was used as an indicator to select transformed petunia cells. Callus was induced from the transformed cells using a conventional method, and then re-differentiated into a plant body.

Example 5
Expression of the PetSPL2 Gene in a PetSPL2 Transformed Plant

Figure 3:
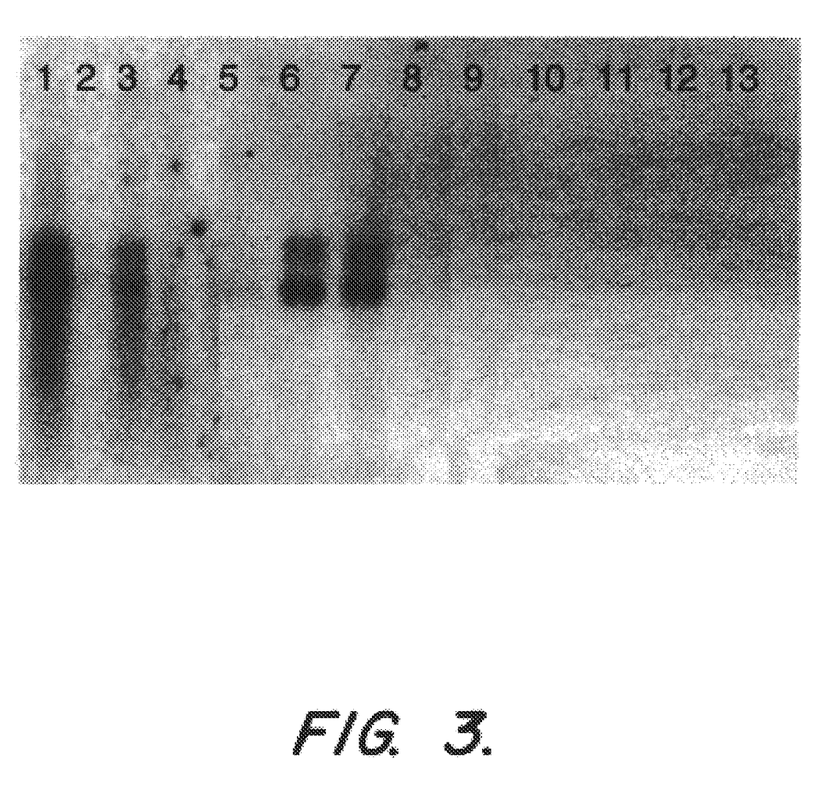
FIG. 3 shows an autoradiogram of a denatured agarose gel electrophoresis image detecting mRNA of the PetSPL2 gene in *Petunia hybrida* transformed with the PetSPL2 gene.

Total RNAs were extracted from leaves of 14 PetSPL2 transformed petunias obtained in Example 4. 10 μg each of the extracts was subjected to denatured agarose gel electrophoresis, and blotted onto a Genescreen plus filter (produced by DuPont) in accordance with a conventional method. A PetSPL2 antisense RNA was labelled using DIG RNA labelling kit (produced by Boeringer Mannheim). Hybridization and filter washing were performed with the labelled RNA according to the instructions of the kit. After the washing, the filter was exposed to an XAR film (produced by Kodak) for 1 hour at room temperature. FIG. 3 shows an autoradiogram of an image of denatured agarose gel electrophoresis which detected PetSPL2 gene mRNAs from 13 petunias. These results indicated that 4 out of 13 individual transformant petunias expressed PetSPL2 mRNA at a high level under the control of a high expression promoter.

Figure 4:
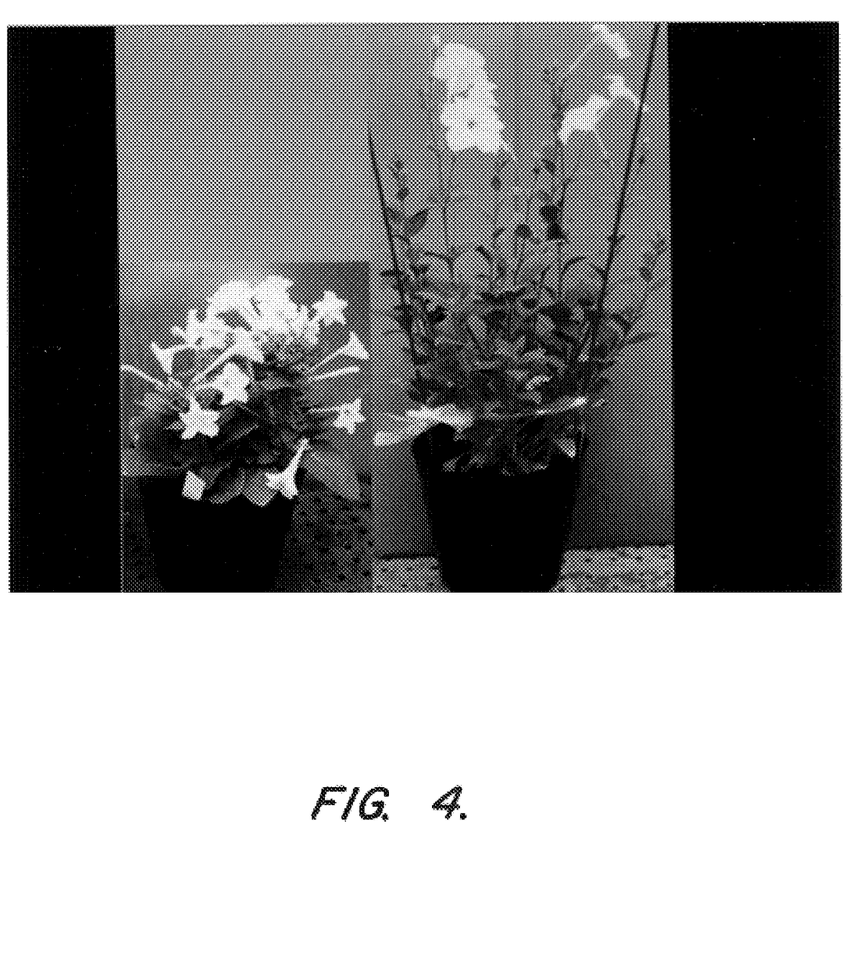
FIG. 4 shows pictures of morphology of a plant body of wild-type *Petunia hybrida* (right) and that of *Petunia hybrida* transformed with the PetSPL2 gene (left).
Figure 5:
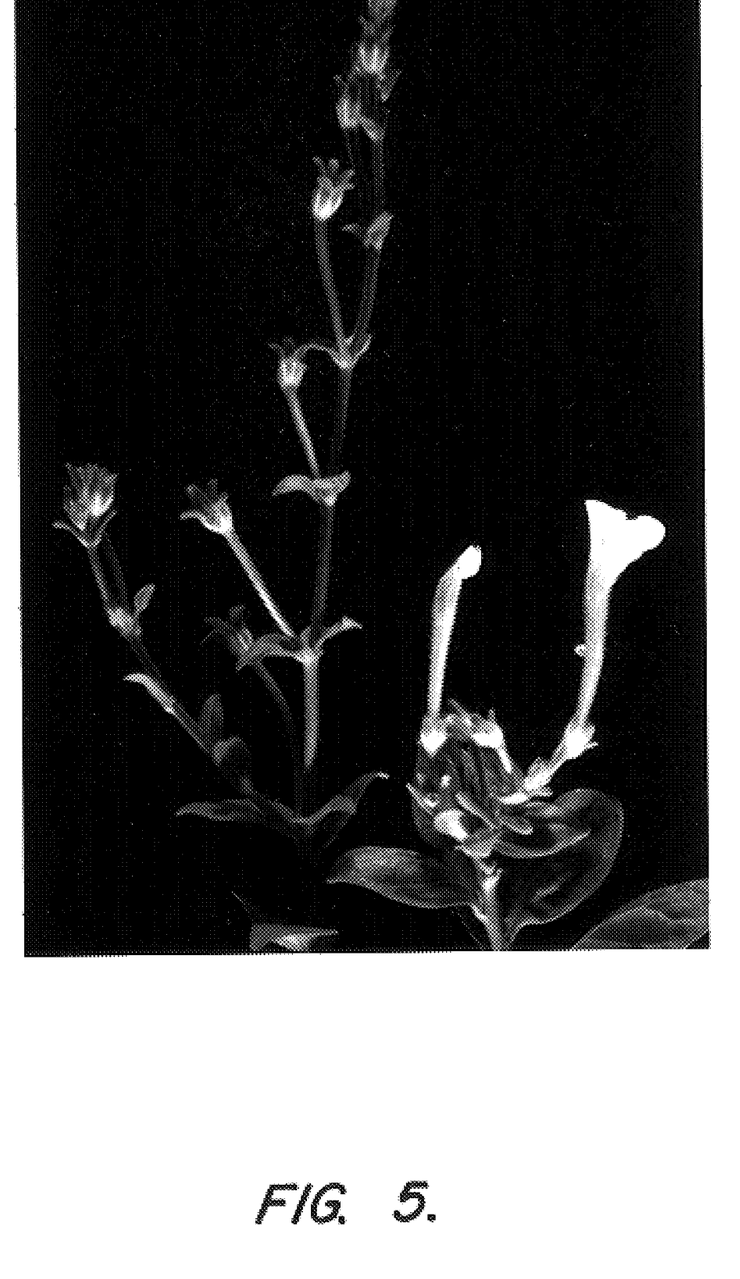
FIG. 5 shows pictures of internodes of wild-type *Petunia hybrida* (left) and those of *Petunia hybrida* transformed with the PetSPL2 gene (right).

Example 6
Phenotype of a Transformant Petunia Expressing PetSPL2 Gene at High Level Phenotypes as described below were commonly observed in 3 petunias out of 4 individual transformant petunias expressing the PetSPL2 gene at high levels. The remaining one petunia expressed the PetPSL2 gene at relatively low level compared with the above three petunias. The most significant change observed in the plant bodies was shortening of the internode length of their inflorescences (i.e., suppression of internode elongation) and dwarfism associated therewith (FIG. 4; left panel shows a PetSPL2-transformant petunia and right panel shows a wild type petunia). This change was observed more extensively in the reproductive stage, namely inflorescence, than in the vegetative stage. The internode length of the inflorescence was shown to be less than one tenth of the wild type (FIG. 5; left panel shows internodes of a wild type petunia and right panel shows those of a PetSPL3-transformant petunia). Other changes were rounding of leaves, a moderate decrease in size of flowers and the like (FIG. 4).

For a gene involved in controlling the internode elongation of inflorescence, an ERECTA gene of *Arabidopsis thaliana* has been reported (Torii et al., 1996, Plant Cell, 8:735). However, no significant homology between the ERECTA gene and the PetSPL2 gene of the present invention is found at either a nucleotide sequence level or an amino acid sequence level. Some of the genes which are involved in plant hormone synthesis and control thereof (rolA, etc.) are also known to shorten the internode length. However, these plant hormone-related genes are known for exhibiting multiple effects as well as controlling the internode elongation (Dehio et al., 1993, *Plant Mol. Bio.*, 23:1199).

From the results described above, it has been shown that the PetSPL2-transformant petunia becomes more dwarfish with shortening of the internode length such that the appearance of the flowers change significantly as compared to the wild types. Accordingly, it is understood that introduction of the PetSPL2 gene is useful, especially for ornamental flowers or horticultral types whose internode length is prone to elongation. A significant change in the appearance of flowers may confer a new value for appreciation on plants. In addition, suppression of the height of a plant may have a significant horticultural value with respect to making the plant resistant to dislodging. Furthermore, fruit trees having the PetSPL gene introduced therein are expected to become compact in their shapes. This is meaningful because it may make fruit-harvesting work more efficient.

According to the present invention, a gene encoding a transcription factor capable of altering morphology, and the like of a plant is provided. By utilizing the present gene, a plant with altered character can be produced. The generated plant is horticulturally useful because it is provided with the character which is not found or rarely found in a wild-type and a horticultural type.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An isolated DNA molecule comprising a nucleotide sequence from the 190th position to the 807th position of the nucleotide sequence represented in SEQ ID NO:1.

2. An isolated DNA molecule encoding a transcription factor comprising an amino acid sequence from the 1st position to the 206th position of the amino acid sequence represented in SEQ ID NO:2.

3. A method for producing a transgenic plant, comprising the steps of:
introducing the DNA molecule of claim 1 into a plant cell; and
regenerating the plant cell into a transgenic plant.

4. A method according to claim 3, wherein the plant is a *dicotyledon*.

5. A method according to claim 4, wherein the plant is a member of the Solanaceae family.

6. A method according to claim 5, wherein the plant is a member of the Petunia genus.

7. A method according to claim 3, wherein the DNA molecule is incorporated into a plant expression vector.

8. A transgenic plant produced by the method of claim 3.

9. A method for producing a transgenic plant, comprising the steps of:
introducing the DNA molecule of claim 2 into a plant cell; and
regenerating the plant cell into a transgenic plant.

10. A transgenic plant produced by the method of claim 9.

11. A method for altering characters of a plant, comprising steps of:
introducing the DNA molecule of claim 1 into a plant cell;
regenerating the plant cell into a transgenic plant; and
selecting the plant having altered characters, wherein the characters of the plant include one selected from the group consisting of the height of the plant and the length of an internode.

12. A method for altering characters of a plant, comprising steps of:
introducing the DNA molecule of claim 2 into a plant cell;
regenerating the plant cell into a transgenic plant; and
selecting the plant having altered characters, wherein the characters of the plant include one selected from the group consisting of the height of the plant and the length of an internode.

* * * * *

SEQUENCE LISTING

```
<160> NUMBER OF SEQ ID NOS: 18

<210> SEQ ID NO 1
<211> LENGTH: 997
<212> TYPE: DNA
<213> ORGANISM: Petunia hybrida var. Mitchell
<220> FEATURE:
<221> NAME/KEY: CDS
<222> LOCATION: (190)..(810)
<223> OTHER INFORMATION: PetSPL2 transcription factor

<400> SEQUENCE: 1
cccagtgcca tttttctct ctagtcaagc tctctatatc atcatcacta ttcccttggc      60
tgcagtaaca ctcctattta accctcacaa aaaaattacc agagggcagc aaaaaatgct    120
tgaacataat tattatactt actattaagc tagatttcct cttgatcttg ctaggtttga    180 ctggagaaa atg gca ggc atg gat aga aac agt ttc aac agt aag tac ttc    231
           Met Ala Gly Met Asp Arg Asn Ser Phe Asn Ser Lys Tyr Phe
             1               5                  10 aaa aac aaa agc atc atg gca aga cag atg gag tac ttg aat aac aac     279
Lys Asn Lys Ser Ile Met Ala Arg Gln Met Glu Tyr Leu Asn Asn Asn
 15                  20                  25                  30 aat ggc gac aat aac aac aac aat aat gtt aca agc tca tta cga gat     327
```

```
Asn Gly Asp Asn Asn Asn Asn Asn Val Thr Ser Ser Leu Arg Asp
                35                  40                  45 aat tat gga aat gaa gat cat tta ctt ggt gga cta ttc tct tgg cct    375
Asn Tyr Gly Asn Glu Asp His Leu Leu Gly Gly Leu Phe Ser Trp Pro
            50                  55                  60 cca aga tct tat aca tgt agc ttt tgt aaa agg gaa ttt aga tct gct    423
Pro Arg Ser Tyr Thr Cys Ser Phe Cys Lys Arg Glu Phe Arg Ser Ala
        65                  70                  75 caa gct ctt ggt gga cac atg aat gtt cat aga aga gat aga gcc att    471
Gln Ala Leu Gly Gly His Met Asn Val His Arg Arg Asp Arg Ala Ile
    80                  85                  90 ttg aga caa tca cca cct aga gat att aat agg tat tct ctt cta aac    519
Leu Arg Gln Ser Pro Pro Arg Asp Ile Asn Arg Tyr Ser Leu Leu Asn
 95                 100                 105                 110 ctt aat ctt gaa cca aac cct aac ttt tac cct agt cat aac cct agt    567
Leu Asn Leu Glu Pro Asn Pro Asn Phe Tyr Pro Ser His Asn Pro Ser
                115                 120                 125 ttt tca aga aaa ttc cca cct ttt gaa atg agg aaa tta gga aaa gga    615
Phe Ser Arg Lys Phe Pro Pro Phe Glu Met Arg Lys Leu Gly Lys Gly
            130                 135                 140 gtt gtt cca aac aat cac ttg aaa agt gcc aga ggg cgt ttt gga gtt    663
Val Val Pro Asn Asn His Leu Lys Ser Ala Arg Gly Arg Phe Gly Val
        145                 150                 155 gag aaa att gac tct ttc atg caa gaa aaa gaa tgt act act aca gtg    711
Glu Lys Ile Asp Ser Phe Met Gln Glu Lys Glu Cys Thr Thr Thr Val
    160                 165                 170 atc aag aag tcc gag ttt cta aga ttg gac ttg gga att ggg ttg atc    759
Ile Lys Lys Ser Glu Phe Leu Arg Leu Asp Leu Gly Ile Gly Leu Ile
175                 180                 185                 190 agt gaa tca aag gaa gat tta gat ctt gaa ctt cga ctg gga tcc act    807
Ser Glu Ser Lys Glu Asp Leu Asp Leu Glu Leu Arg Leu Gly Ser Thr
                195                 200                 205 taactatatc taattttac ggcattaagg tttgtaaatt gagtcgacag cttagtcaaa    867
actacttatg cactttaata tggcttcttg tgctatattt atttatttta catggctgta    927
tctaggtttg catttaaga tttagtacct tgtcagatta aagaaaacg aaagttaaat    987 taaaaaaaaa                                                         997

<210> SEQ ID NO 2
<211> LENGTH: 206
<212> TYPE: PRT
<213> ORGANISM: Petunia sp.

<400> SEQUENCE: 2

Met Ala Gly Met Asp Arg Asn Ser Phe Asn Ser Lys Tyr Phe Lys Asn
  1               5                  10                  15

Lys Ser Ile Met Ala Arg Gln Met Glu Tyr Leu Asn Asn Asn Asn Gly
            20                  25                  30

Asp Asn Asn Asn Asn Asn Val Thr Ser Ser Leu Arg Asp Asn Tyr
        35                  40                  45

Gly Asn Glu Asp His Leu Leu Gly Gly Leu Phe Ser Trp Pro Pro Arg
    50                  55                  60

Ser Tyr Thr Cys Ser Phe Cys Lys Arg Glu Phe Arg Ser Ala Gln Ala
 65                 70                  75                  80

Leu Gly Gly His Met Asn Val His Arg Arg Asp Arg Ala Ile Leu Arg
                85                  90                  95

Gln Ser Pro Pro Arg Asp Ile Asn Arg Tyr Ser Leu Leu Asn Leu Asn
            100                 105                 110
```

```
Leu Glu Pro Asn Pro Asn Phe Tyr Pro Ser His Asn Pro Ser Phe Ser
        115                 120                 125

Arg Lys Phe Pro Pro Phe Glu Met Arg Lys Leu Gly Lys Gly Val Val
    130                 135                 140

Pro Asn Asn His Leu Lys Ser Ala Arg Gly Arg Phe Gly Val Glu Lys
145                 150                 155                 160

Ile Asp Ser Phe Met Gln Glu Lys Glu Cys Thr Thr Thr Val Ile Lys
                165                 170                 175

Lys Ser Glu Phe Leu Arg Leu Asp Leu Gly Ile Gly Leu Ile Ser Glu
            180                 185                 190

Ser Lys Glu Asp Leu Asp Leu Glu Leu Arg Leu Gly Ser Thr
        195                 200                 205

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:degenerate
      primer 1
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i

<400> SEQUENCE: 3
cargcnytng gnggncay                                              18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:degenerate
      primer 2
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i

<400> SEQUENCE: 4
ytnggnggnc ayatgaay                                              18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:degenerate
```

```
            primer 3
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i

<400> SEQUENCE: 5
arncknaryt cnarrtc                                               17

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:amino acids
      present in both SUPERMAN gene of Arabidopsis
      thaliana and GmN479 gene of soy bean root nodules

<400> SEQUENCE: 6

Gln Ala Leu Gly Gly His
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:amino acids
      present in both SUPERMAN gene of Arabidopsis
      thaliana and GmN479 gene of soy bean root nodules

<400> SEQUENCE: 7

Leu Gly Gly His Met Asn
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:amino acids
      present in both SUPERMAN gene of Arabidopsis
      thaliana and GmN479 gene of soy bean root nodules

<400> SEQUENCE: 8

Asp Leu Glu Leu Arg Leu
 1               5

<210> SEQ ID NO 9
<211> LENGTH: 43
<212> TYPE: PRT
<213> ORGANISM: Artificial Sequence
<220> FEATURE:
<223> OTHER INFORMATION: Description of Artificial Sequence:SUPERMAN
      zinc finger motif

<400> SEQUENCE: 9

Ser Tyr Thr Cys Ser Phe Cys Lys Arg Glu Phe Arg Ser Ala Gln Ala
 1               5                  10                  15

Leu Gly Gly His Met Asn Val His Arg Arg Asp Arg Ala Arg Leu Arg
                20                  25                  30
```

Leu Gln Gln Ser Pro Ser Ser Ser Ser Thr Pro
         35                  40

<210> SEQ ID NO 10
<211> LENGTH: 42
<212> TYPE: PRT
<213> ORGANISM: Artificial Sequence
<220> FEATURE:
<223> OTHER INFORMATION: Description of Artificial Sequence:PetSPL1 zinc
      finger motif

<400> SEQUENCE: 10

Ser Tyr Thr Cys Ser Phe Cys Lys Arg Glu Phe Arg Ser Ala Gln Ala
 1               5                  10                  15

Leu Gly Gly His Met Asn Val His Arg Arg Asp Arg Ala Arg Leu Arg
             20                  25                  30

Leu Gln Ser Pro Pro Arg Glu Asn Gly Thr
         35                  40

<210> SEQ ID NO 11
<211> LENGTH: 41
<212> TYPE: PRT
<213> ORGANISM: Artificial Sequence
<220> FEATURE:
<223> OTHER INFORMATION: Description of Artificial Sequence:PetSPL2 zinc
      finger motif

<400> SEQUENCE: 11

Ser Tyr Thr Cys Ser Phe Cys Lys Arg Glu Phe Arg Ser Ala Gln Ala
 1               5                  10                  15

Leu Gly Gly His Met Asn Val His Arg Arg Asp Arg Ala Ile Leu Arg
             20                  25                  30

Gln Ser Pro Pro Arg Asp Ile Asn Arg
         35                  40

<210> SEQ ID NO 12
<211> LENGTH: 43
<212> TYPE: PRT
<213> ORGANISM: Artificial Sequence
<220> FEATURE:
<223> OTHER INFORMATION: Description of Artificial Sequence:PetSPL3 zinc
      finger motif

<400> SEQUENCE: 12

Ser Tyr Glu Cys Asn Phe Cys Lys Arg Gly Phe Ser Asn Ala Gln Ala
 1               5                  10                  15

Leu Gly Gly His Met Asn Ile His Arg Lys Asp Lys Ala Lys Leu Lys
             20                  25                  30

Lys Gln Lys Gln His Gln Arg Gln Gln Lys Pro
         35                  40

<210> SEQ ID NO 13
<211> LENGTH: 43
<212> TYPE: PRT
<213> ORGANISM: Artificial Sequence
<220> FEATURE:
<223> OTHER INFORMATION: Description of Artificial Sequence:PetSPL4 zinc
      finger motif

<400> SEQUENCE: 13

Phe Tyr Arg Cys Ser Phe Cys Lys Arg Gly Phe Ser Asn Ala Gln Ala
 1               5                  10                  15

Leu Gly Gly His Met Asn Ile His Arg Lys Asp Arg Ala Lys Leu Arg

```
                    20                  25                  30
Glu Ile Ser Thr Asp Asn Leu Asn Ile Asp Gln
            35                  40

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence:SUPERMAN
      C-terminal hydrophobic region

<400> SEQUENCE: 14

Ile Leu Arg Asn Asp Glu Ile Ile Ser Leu Glu Leu Glu Ile Gly Leu
 1               5                  10                  15

Ile Asn Glu Ser Glu Gln Asp Leu Asp Leu Glu Leu Arg Leu Gly Phe
            20                  25                  30

Ala

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence:PetSPL1
      C-terminal hydrophobic region

<400> SEQUENCE: 15

Leu Met Lys Arg Ser Glu Phe Leu Arg Leu Glu Leu Gly Ile Gly Met
 1               5                  10                  15

Ile Asn Glu Ser Lys Glu Asp Leu Asp Leu Glu Leu Arg Leu Gly Tyr
            20                  25                  30

Thr

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence:Pet SPL2
      C-terminal hydrophobic region

<400> SEQUENCE: 16

Val Ile Lys Lys Ser Glu Phe Leu Arg Leu Asp Leu Gly Ile Gly Leu
 1               5                  10                  15

Ile Ser Glu Ser Lys Glu Asp Leu Asp Leu Glu Leu Arg Leu Gly Ser
            20                  25                  30

Thr

<210> SEQ ID NO 17
<211> LENGTH: 33
<212> TYPE: PRT
<213> ORGANISM: Artificial Sequence
<220> FEATURE:
<223> OTHER INFORMATION: Description of Artificial Sequence:PetSPL3
      C-terminal hydrophobic region

<400> SEQUENCE: 17

Gly Ser Val Asp Ser Arg Glu Asn Arg Leu Pro Ala Arg Asn Gln Glu
 1               5                  10                  15

Thr Thr Pro Phe Tyr Ala Glu Leu Asp Leu Glu Leu Arg Leu Gly His
            20                  25                  30
```

```
Glu

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence:PetSPL4
      C-terminal hydrophobic region

<400> SEQUENCE: 18

Cys Gly Thr Leu Asp Glu Lys Pro Lys Arg Gln Ala Glu Asn Asn Asp
 1               5                  10                  15

Met Gln Gln Asp Asp Ser Lys Leu Asp Leu Glu Leu Arg Leu Gly Pro
            20                  25                  30

Asp
```